(12) United States Patent
Ambrus et al.

(10) Patent No.: US 8,629,185 B2
(45) Date of Patent: Jan. 14, 2014

(54) 7-[3,5-DIHYDROXY-2- (3-HYDROXY-5-PHENYL-PENT-1-ENYL)-CYCLOPENTYL]-N-ETHYL-HEPT-5-ENAMIDE (BIMATOPROST) IN CRYSTALLINE FORM II, METHODS FOR PREPARATION, AND METHODS FOR USE THEREOF

(75) Inventors: Gyorgy F. Ambrus, Santa Ana, CA (US); Kiomars Karami, Aliso Viejo, CA (US); Ke Wu, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 235 days.

(21) Appl. No.: 12/951,780

(22) Filed: Nov. 22, 2010

(65) Prior Publication Data
US 2011/0152376 A1    Jun. 23, 2011

Related U.S. Application Data

(60) Provisional application No. 61/263,471, filed on Nov. 23, 2009.

(51) Int. Cl.
*A61K 31/165* (2006.01)
*A61P 27/02* (2006.01)
*C07C 235/34* (2006.01)

(52) U.S. Cl.
USPC .......................................... 514/622; 564/171

(58) Field of Classification Search
USPC .......................................... 514/622; 564/171
See application file for complete search history.

(56) References Cited

U.S. PATENT DOCUMENTS

| 2005/0209337 | A1 | 9/2005 | Gutman |
| 2009/0163596 | A1 | 6/2009 | Gutman |

OTHER PUBLICATIONS

Bito, L. Z., Biological Protection with Prostanoids, CRC Press, Inc., Jan. 1, 1985, 1, pp. 231-252, Cohen, M. M., ed., Boca Raton, Fla., CRC Press Inc.
Bito, L. Z, Applied Pharmacology in the Medical Treatment of Glaucomas Drance, Glaucoma: Applied Pharmacology, Jan. 1, 1984, 20, pp. 477-505, S. M. and Neufeld, A. H. eds., New York, Grune & Stratton.
Starr, Further Studies on the Effects of Prostagladin on Intraocular Pressure in the Rabbit, Department of Physiology and Biochemistry, Institute of Ophthalmology, 1971, 11, 170-177, exp. Eye Res.

*Primary Examiner* — Sreeni Padmanabhan
*Assistant Examiner* — Irina Neagu
(74) *Attorney, Agent, or Firm* — Krishna Banerjee; Debra D. Condino

(57) ABSTRACT

The present invention provides a new crystalline form of bimatoprost, designated as crystalline form II. This new crystalline form is the most stable form known to date of bimatoprost. Moreover, it has been found that bimatoprost crystalline form II is readily prepared from crystalline form I.

7 Claims, 7 Drawing Sheets

Thermograms of two lots of Bimatoprost (Lot X10510 representative of all the lots except for Lot 08-A-014-3)

Polymorph I (Lot X10510)

A mixture of Polymorphs I and II (Lot 08-A-014-3)

Thermogram of the discussed sample treatment cycle consisting of the partial melting and controlled cooling of Lot 08-A-014-3

Thermogram of Lot 08-A-014-3 after partial melting and controlled cooling demonstrates the presence of pure Polymorph II Thermogram of stress stability sample 1 of lot X10510 subjected to 40°C, ambient air headspace and light exposure Thermogram of stress stability sample 2 of lot X10510 subjected to 40°C, ambient air headspace and protected from light exposure ём# 7-[3,5-DIHYDROXY-2-(3-HYDROXY-5-PHENYL-PENT-1-ENYL)-CYCLOPENTYL]-N-ETHYL-HEPT-5-ENAMIDE (BIMATOPROST) IN CRYSTALLINE FORM II, METHODS FOR PREPARATION, AND METHODS FOR USE THEREOF

CROSS REFERENCE TO RELATED APPLICATIONS

This application claims the benefit of U.S. Provisional Application Ser. No. 61/263,471 filed on Nov. 23, 2009, which is hereby incorporated by reference in its entirety.

FIELD OF THE INVENTION

The present invention relates generally to crystalline forms of 7-[3,5-dihydroxy-2-(3-hydroxy-5-phenyl-pent-1-enyl)-cyclopentyl]-N-ethyl-hept-5-enamide (bimatoprost) and particularly to a newly identified crystalline form of bimatoprost. The present invention further relates to methods for its preparation and to methods for treating disorders associated with ocular hypertension.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla. CRC Press Inc., 1985, pp. 231-252; and Bito, L. Z., Applied Pharmacology in the Medical Treatment of Glaucomas Drance, S. M. and Neufeld, A. H. eds., New York, Grune & Stratton, 1984, pp. 477-505). Such prostaglandins include $PGF_{2\alpha}$, $PGF_{1\alpha}$ $PGE_2$, and certain lipid-soluble esters, such as $C_1$ to $C_5$ alkyl esters, e.g. 1-isopropyl ester, of such compounds.

It is known however that many drug compounds exist in two or more crystalline forms, referred to as polymorphs. These polymorphs of the same molecule have identical chemical properties but may exhibit different physical properties, such as melting point, solubility, hardness, etc. In such cases, the danger exists of less soluble polymorphic forms precipitating from a solution made from another more soluble but less stable form. The formation of crystals in an ophthalmic solution can cause serious injury to the eye. In addition, precipitation of the drug substance may cause an apparent reduction in potency and bioavailability of the product.

For these reasons, there has been interest in the polymorphic forms of bimatoprost (currently marketed as Lumigan™). U.S. Patent Application Publication No. 2009/0163596 describes bimatoprost in crystalline form I. The present invention describes a new polymorphic form of bimatoprost.

SUMMARY OF THE INVENTION

The present invention provides a new crystalline form of 7-[3,5-dihydroxy-2-(3-hydroxy-5-phenyl-pent-1-enyl)-cyclopentyl]-N-ethyl-hept-5-enamide (bimatoprost), designated as crystalline form II. This new crystalline form is the most stable form known to date of bimatoprost. Moreover, it has been found that bimatoprost crystalline form II is readily prepared from crystalline form I or may be prepared directly from amorphous bimatoprost.

In another embodiment of the invention, there provided pharmaceutical compositions including a therapeutically effective amount of 7-[3,5-dihydroxy-2-(3-hydroxy-5-phenyl-pent-1-enyl)-cyclopentyl]-N-ethyl-hept-5-enamide in crystalline form II in an ophthalmically acceptable carrier therefore.

In another embodiment, there provided methods for treating ocular hypertension Such methods can be performed, for example, by administering to a subject in need thereof 7-[3,5-dihydroxy-2-(3-hydroxy-5-phenyl-pent-1-enyl)-cyclopentyl]-N-ethyl-hept-5-enamide in crystalline form II in an ophthalmically acceptable carrier.

In another embodiment, there provided methods for treating glaucoma. Such methods can be performed, for example, by administering to a subject in need thereof 7-[3,5-dihydroxy-2-(3-hydroxy-5-phenyl-pent-1-enyl)-cyclopentyl]-N-ethyl-hept-5-enamide in crystalline form II in an ophthalmically acceptable carrier.

In another embodiment of the invention there provided methods for converting 7-[3,5-dihydroxy-2-(3-hydroxy-5-phenyl-pent-1-enyl)-cyclopentyl]-N-ethyl-hept-5-enamide in crystalline form I to crystalline form II. Such methods can be performed, for example, by
a) heating 7-[3,5-dihydroxy-2-(3-hydroxy-5-phenyl-pent-1-enyl)-cyclopentyl]-N-ethyl-hept-5-enamide in crystalline form I in the solid state from about 55° C. to about 72° C. at a heating rate of about 2° C. per minute;

b) cooling the crystalline 7-[3,5-dihydroxy-2-(3-hydroxy-5-phenyl-pent-1-enyl)-cyclopentyl]-N-ethyl-hept-5-enamide from about 72° C. to about 55° C. at a heating rate of about 0.2-0.5° C. per minute;

c) repeating steps a) and b) from 3 to about 9 times;

thereby converting crystalline form I to crystalline form II.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

It is to be understood that "7-[3,5-dihydroxy-2-(3-hydroxy-5-phenyl-pent-1-enyl)-cyclopentyl]-N-ethyl-hept-5-enamide" and "bimatoprost" refer to the same compound and may be used interchangeably throughout.

In addition, it is to be understood that "crystalline form" and "polymorphic form" may be used interchangeably throughout the specification. "Crytalline form I" or "crystalline form II" may also be referred to as "polymorph I" or "polymorph II".

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation The present invention provides bimatoprost in a new polymorphic form, designated as polymorph II. This new, more stable polymorph was discovered by exposing polymorph I to elevated temperatures and humidities. During these studies it was found that polymorph I converts quantitatively to polymorph II by using the controlled heating and cooling cycles set forth herein.

Bimatoprost crystalline form II was characterized using X-ray powder diffraction (XRPD), differential scanning calorimetry (DSC), and infrared spectroscopy.

Figure 2:
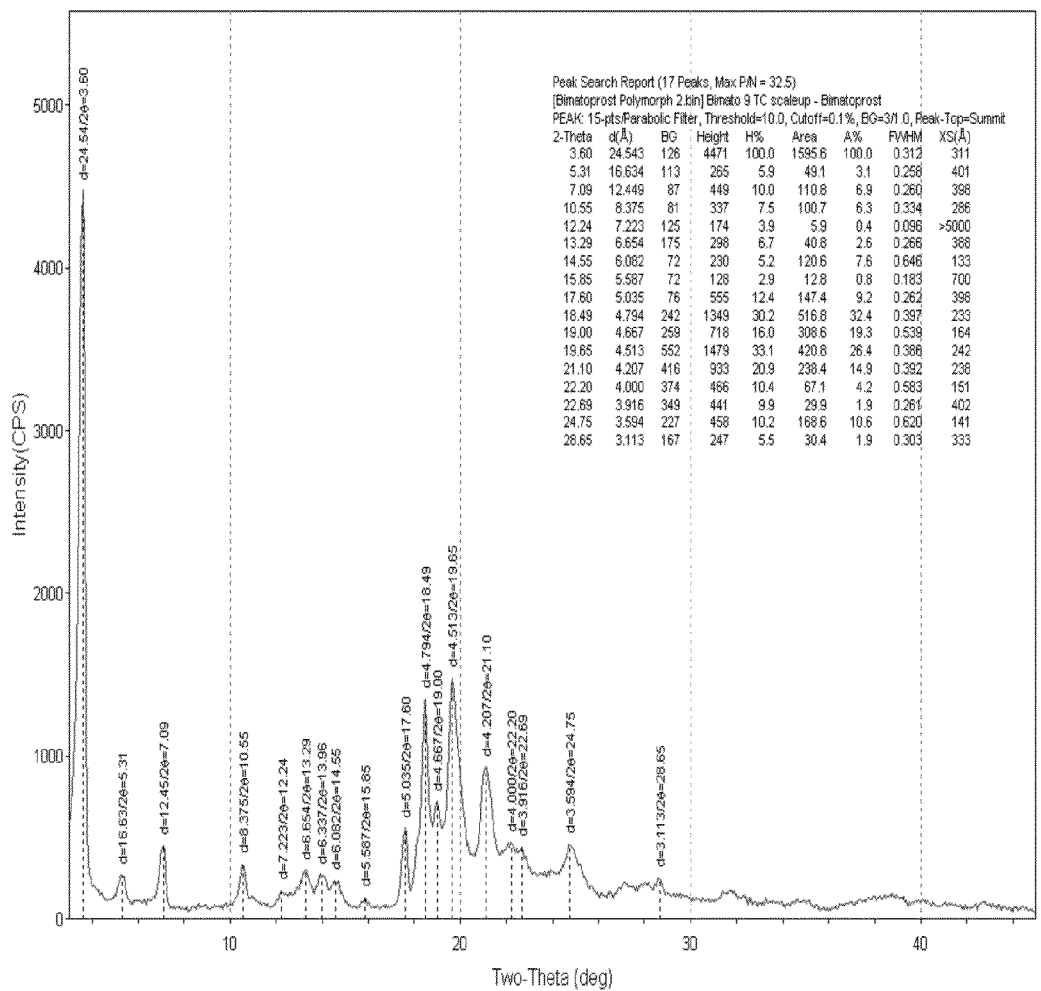
FIG. 2 is a characteristic X-ray powder diffraction (XRPD) pattern of bimatoprost in crystalline form II.

The crystalline form II of bimatoprost exhibits a distinct XRPD spectrum, which is set forth in FIG. 2. The pattern has characteristic peaks observed at (2θ): 3.60, 5.31, 7.09, 10.55, 12.24, 13.29, 14.55, 15.85, 17.60, 18.49, 19.00, 19.65, 21.10, 22.20, 22.69, 24.75 and 28.65.

Polymorph II was determined to have an endothermic onset at about 70.9° C. and a peak at 74.5° C. in its differential scanning calorimetry profile.

In another embodiment of the invention, there is provided a method for converting bimatoprost polymorph I to bimatoprost polymorph II.

Conventional methods of making a desired polymorph include: modifying crystallization conditions (temperature, solvent, etc) stirring a suspension of polymorph I in various organic solvents (aka slurry method); and, adding seed crystals of polymorph II into a suspension of polymorph I. Solvents are used in these methods allowing sufficient molecular motions that promote nucleation to the different polymorph. When slurry studies were conducted with bimatoprost polymorph I using water, ethyl acetate, or cyclohexane to produce polymorph II, the final product was an oily residue. The same result was obtained when seed crystals of polymorph II were added to the suspension. When slurries containing polymorph I were repeatedly heated and cooled, which is a common technique used to promote crystallization, no crystals of polymorph II were produced.

The method of the invention involves heating and cooling the neat drug substance in the solid state. This method is unique because solvents are not used to promote molecular mobility and subsequent nucleation. Bimatoprost polymorph I in the solid state (20 mg) was heated from 55° C. to 72° C. at a heating rate of 2° C./min followed by cooling from 72° C. to 55° C. at a rate of 0.2-0.5° C./min. The cycle was repeated 3-9 times. Polymorph I was converted to polymorph II. Formation of polymorph II was confirmed by DSC and XRPD (see Examples).

Pharmaceutical compositions may be prepared by combining a therapeutically effective amount of polymorph II of bimatoprost according to the invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydrox ypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

Ingredient Amount (% w/w) active ingredient about 0.001-5 preservative 0-0.10 vehicle 0-40 tonicity adjustor 0-10 buffer 0.01-10 pH adjustor q.s. pH 4.5-7.5 antioxidant as needed surfactant as needed purified water as needed to make 100%

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 ml.

The following examples are intended only to illustrate the present invention and should in no way be construed as limiting the subject invention.

EXAMPLES

Screening Lots of Bimatoprost for Polymorphs

Figure 3:
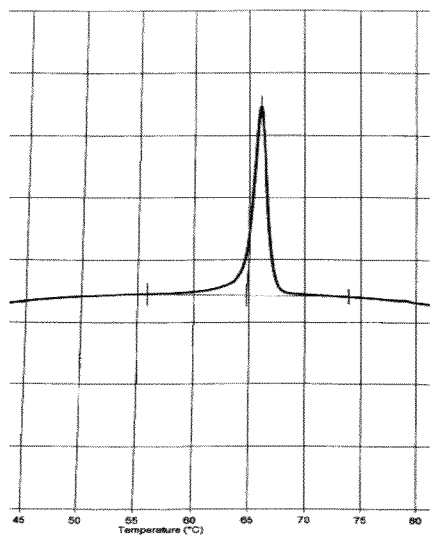
FIG. 3 depicts thermograms of two lots of bimatoprost (Lot X10510 representative of all the lots except for Lot 08-A-014-3).
Figure 3:

Twenty-one (21) lots of bimatoprost, representative of three evolving manufacturing processes, were screened for polymorphs by differential scanning calorimetry (Perkin Elmer Thermal Analysis DSC-7). Each lot was analyzed in the same temperature range, from 30° C. to 85° C., at heating rates of 1.0° C. and 2.0° C. per minute. The results included the measured heat of fusion (ΔH), onset and peak temperature. All lots showed consistent results, except for one of the lots that exhibited a second thermal transition (DSC peak) at a higher temperature (see FIG. 3).

Table 1 exemplifies the results obtained and includes the lot (08-A-014-3) that yielded a different result from all other lots.

TABLE 1

Representative lots of Bimatoprost analyzed by DSC between 30° C. and 85° C. at a heating rate of 2° C./minute

| Bimatoprost lot# | Manufacturing process | ΔH (J/g) | Onset (° C.) | Peak (° C.) |
|---|---|---|---|---|
| 91110 | 1 | 53.0 | 61.1 | 65.0 |
| X10510 | 2 | 62.4 | 64.8 | 66.3 |
| X11192 | 3 | 61.2 | 65.1 | 66.8 |
| 08-A-014-3 | 3 | 27.7 | 64.9 | 66.3 |
| 08-A-014-3 | 3 | 48.4 | 71.1 | 73.7 |

Lot #X11192 is the current secondary reference standard. All lots tested showed comparable results to the bimatoprost crystalline form I, except for the one that yielded two thermal transitions. Lot #08-A-014-3 showed two thermal peaks, at 66.3° C. and 73.7° C. The 66.3° C. peak was similar to the other 20 lots of bimatoprost and is referred to as polymorph I. The 73.7° C. peak (thermal transition) was not observed in the other lots. The crystal form that caused the second thermal transition is referred to as polymorph II. The identity of polymorph II was confirmed by additional experiments.

The Confirmation of the Identity of Polymorph II

Figure 4:
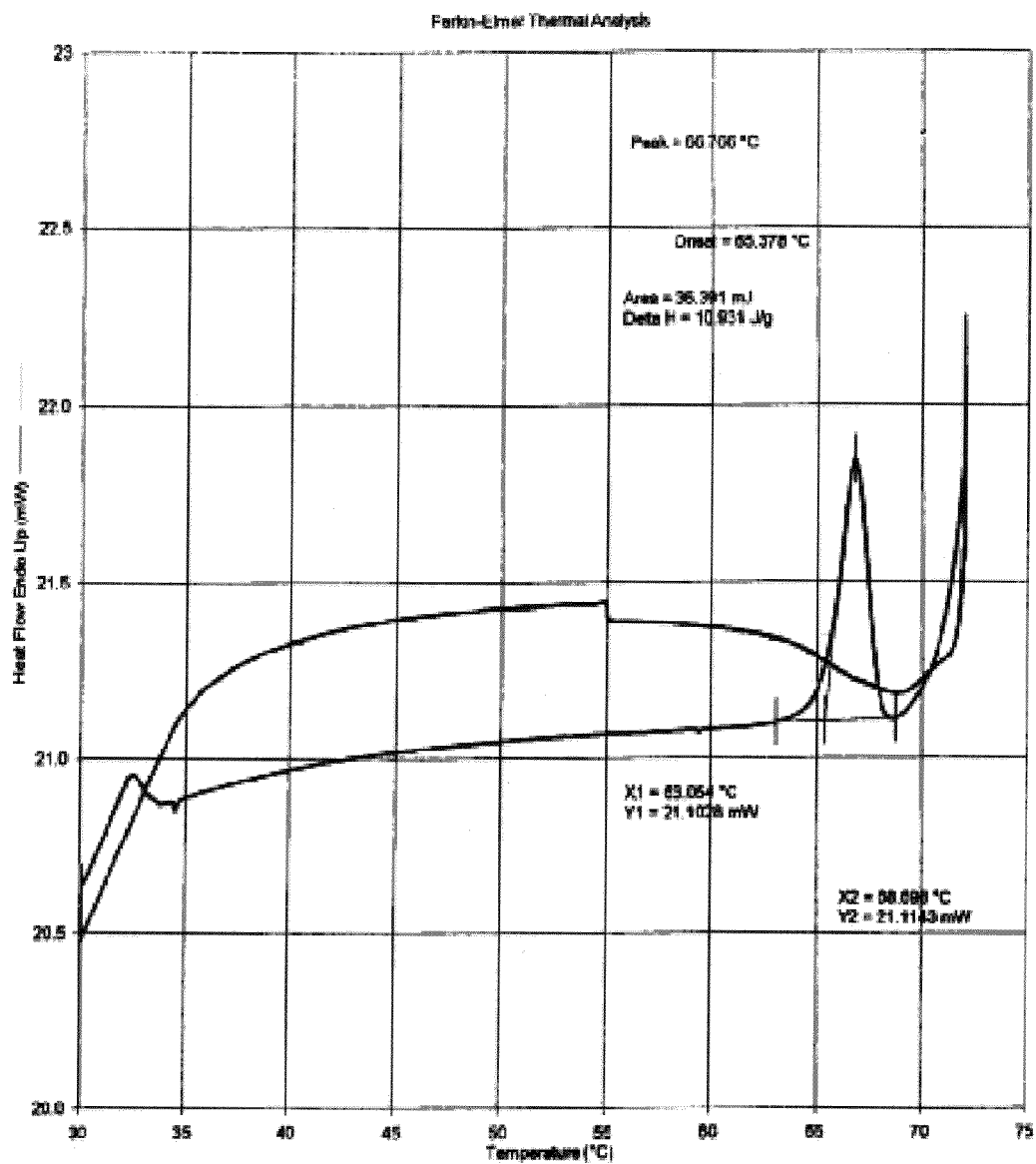
FIG. 4 depicts a thermogram of a sample treatment cycle consisting of the partial melting and controlled cooling of Lot 08-A-014-3.

The confirmation of the identity of Polymorph II was carried out by following experiments:

A representative portion of lot 08-A-014-3 was subjected to controlled melting in a covered DSC pan with a loosely fitting lid (to avoid pressure build-up). The sample was heated at a rate of 2.0° C. per minute to 72° C. (where all of polymorph I melted and polymorph II partially melted, so the melted portion was in contact with pure polymorph II solid). At that point the partially melted sample was subjected to controlled cooling at a rate of 0.5° C. and 1.0° C. per minute (see FIG. 4).

Figure 5:
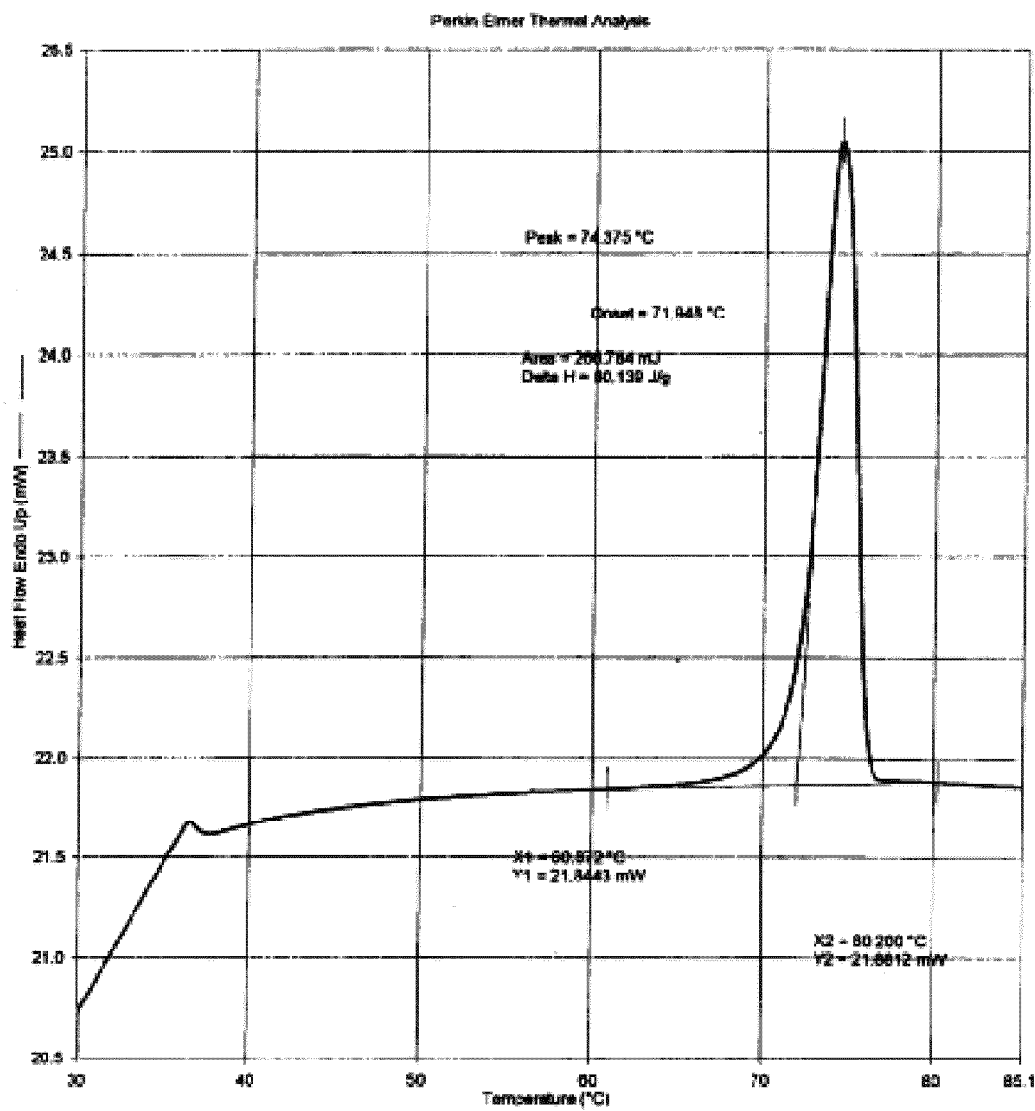
FIG. 5 depicts a thermogram of Lot 08-A-014-3 after partial melting and controlled cooling and demonstrates the presence of pure Polymorph II.

When the sample reached 30° C., in the cooling phase, the material presumably would be fully crystallized as polymorph II. To confirm this hypothesis, the freshly cooled sample was scanned again at a heating rate of 2.0° C. per minute, between 30° C. and 85° C. (see FIG. 5). Using Temperature Program 2, only one thermal transition was found in the sample of lot 08-A-014-3 that had been subjected to Temperature Program 1. The increased melting point indicates that polymorph I converted to the higher melting (and presumably more stable) crystal structure, polymorph II. The temperature programs described in this section are summarized as follows:

Temperature Program 1 (Partial Melting):

1. Hold for 1.0 minute at 30° C.
2. Heat from 30° C. to 72° C. at 2.0° C./minute
3. Hold for 1.0 minute at 72° C.
   (note: 73-74° C. is the apex of the peak representing the melting of Polymorph II)
4. Cool from 72° C. to 55° C. at 0.5° C./minute
5. Cool from 55° C. to 30° C. at 1.0° C./minute Temperature Program 2 (Complete Melting):

1. Hold for 1.0 minute at 30° C.
2. Heat from 30° C. to 85° C. at 2.0° C./minute The results are shown in Table 2.

TABLE 2

Results of lot 08-A-014-3 after Temperature Programs 1 and 2

| Sample | Onset (° C.) | Peak (° C.) |
|---|---|---|
| Polymorph I (08-A-014-3) | 65.4 | 66.8 |
| Polymorph II (08-A-014-3) | 71.9 | 74.4 |

The lot (08-A-014-3) that was subjected to the DSC temperature programs specified above was analyzed by HPLC, and the chromatographic results were compared to those obtained from the control sample (stored at −20° C.) of the same lot. The chromatographic comparison showed that the sample subjected to a partial melting followed by a complete melting was intact bimatoprost having an impurity profile essentially the same as that of the control (frozen) sample.

Since polymorph II was confirmed and identified as bimatoprost, subsequently released bimatoprost lots were also analyzed by DSC. The results showed that only polymorph I was contained in these lots.

Bimatoprost samples representing fourteen (14) lots were submitted for X-ray powder diffraction analysis to SSCI, Inc. (3065 Kent Avenue, West Lafayette, Ind. 47906). According to SSCI analysis, the results showed that the patterns of all samples, except lot 08-A-014-3, were similar to each other in terms of peak positions, suggesting that these samples were the same morphological form. The pattern of lot 08-A-014-3 contained additional reflections, suggesting that this sample was either a mixture of forms or a second crystalline form. The DSC and HPLC results support the conclusion that lot 08-A-014-3 was a mixture of the two polymorphic forms of bimatoprost.

Recrystallization of Bimatoprost

Bimatoprost lot #X11113 was used in the recrystallization study. It was recrystallized using seven solvent systems:
1 dichloromethane/hexane
2 chloroform
3 chloroform/toluene
4 chloroform/hexane
5 ethyl acetate
6 dichloromethane
7 chloroform/pentane A sample isolated from each solvent system was analyzed by DSC. The results showed the exclusive presence of polymorph I in all samples. HPLC assays were also done for each recrystallized sample, and the assay results are shown in Table 3.

The chromatographic results of the recrystallized samples were comparable to those of the corresponding controls (before recrystallization). An increase in the 15-keto levels was the likely result of exposure of the samples to ambient air during the recrystallization experiments. No attempt was made to protect the samples from ambient conditions (temperature, air, humidity, light) during the recrystallization experiments. The bimatoprost assay values remained above 97% w/w, and the overall results indicated that the recrystallization process did not substantially degrade the samples.

Solid-State Polymorphic Transformation in Samples of the Formal Stability Program Upon routine visual examination, one of the Bimatoprost samples (lot X10510) in formal stability showed an amber-colored particle embedded in a larger rock of white active pharmaceutical ingredient (API). DSC and IR analyses confirmed that sample X10510 stored 18 months at 25° C./60% RH yielded substantial amounts of polymorph II. The colored particle was separated from the white drug substance, and DSC was performed on both. The results are shown in Table 4.

TABLE 4

Calorimetric results of the white and the colored Bimatoprost particles found in lot X10510 at 25° C./60% RH (at 18 months)

| Particle | ΔH (J/g) | Onset (° C.) | Peak (° C.) |
|---|---|---|---|
| White | 75.6 | 70.2 | 73.0 |
| Colored | 73.3 | 70.4 | 73.4 |

The particles were assayed by HPLC and the results confirmed that they were intact bimatoprost. The same samples were submitted for solid-state IR spectral analysis. The results of the spectroscopic investigation confirmed that the white and colored particles had no substantial chemical or morphological differences. A comparison of the spectra of these samples with that of the control indicated some distinct differences in crystal habit.

In order to determine whether bimatoprost spontaneously converts from polymorph I to polymorph II at elevated temperatures (i.e. higher than the prescribed storage temperature), a number of other lots in the formal stability program were also analyzed by DSC. The results are summarized in Table 5.

TABLE 3

HPLC Assay Results of Recrystallized Bimatoprost Samples

| | | Impurity (area %) | | | |
|---|---|---|---|---|---|
| Sample recrystallized from system indicated | Bimatoprost (% w/w) | Total unspecified | 15-β isomer | 5,6-trans isomer | 15-keto analog |
| X11113 control | 98.17 | 0.04 | 0.44 | 0.28 | 0.22 |
| dichloromethane/hexane | 97.76 | 0.16 | 0.20 | 0.21 | 0.40 |
| chloroform | 97.06 | 0.40 | 0.27 | 0.25 | 0.76 |
| chloroform/toluene | 97.63 | 0.50 | 0.32 | 0.16 | 0.41 |
| chloroform/hexane | 97.56 | 0.43 | 0.24 | 0.23 | 0.81 |
| ethyl acetate | 97.44 | 0.22 | 0.25 | 0.22 | 0.53 |
| dichloromethane | 97.78 | 0.24 | 0.21 | 0.21 | 0.40 |
| chloroform/pentane | 97.39 | 0.29 | 0.29 | 0.22 | 0.55 |

TABLE 5

Calorimetric results of representative samples in the formal stability program

| Sample lot | Stability condition | Time point (months) | Particle type | ΔH (J/g) | Onset (° C.) | Peak (° C.) |
| --- | --- | --- | --- | --- | --- | --- |
| X10510 | 40° C./75% RH | 3 | white | 69.2 | 67.4 | 71.5 |
| X11113 | 40° C./75% RH | 3 | white | 67.0 | 69.3 | 72.5 |
| X10554 | 25° C./60% RH | 18 | white | 79.8 | 70.6 | 73.1 |
|  |  |  | translucent | 78.5 | 70.9 | 73.9 |

All the formal stability samples tested consisted of polymorph II. Since the control (frozen) samples from the same lots were previously analyzed by DSC with the results showing that none of them contained polymorph II, there is a clear indication that a polymorphic transformation had occurred under the stability conditions employed.

Solid-State Polymorphic Transformation in Laboratory Stress Study Samples

Figure 6:
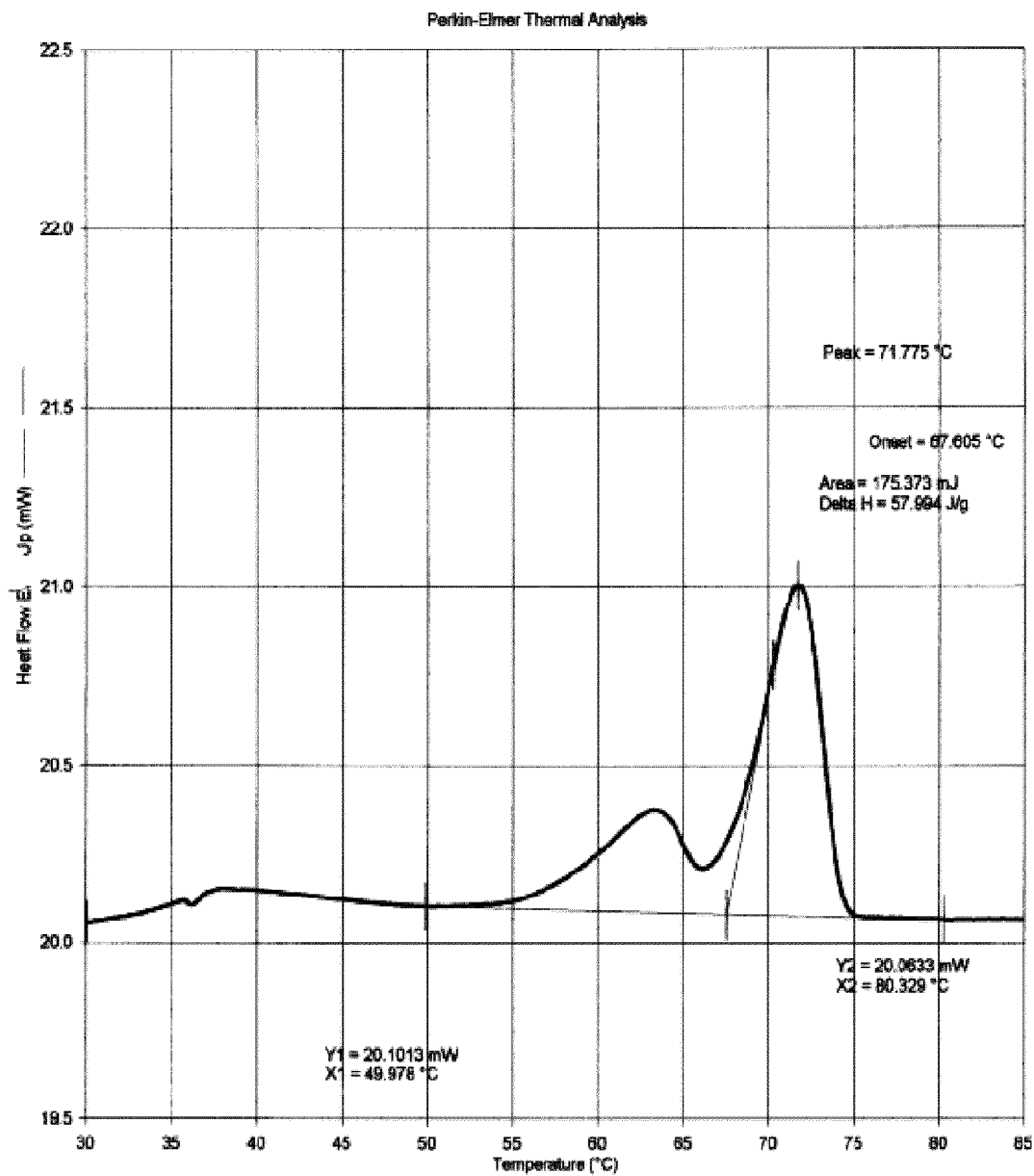
FIG. 6 depicts a thermogram of stress stability sample 1 of lot X10510 subjected to 40° C., ambient air headspace and light exposure.
Figure 7:
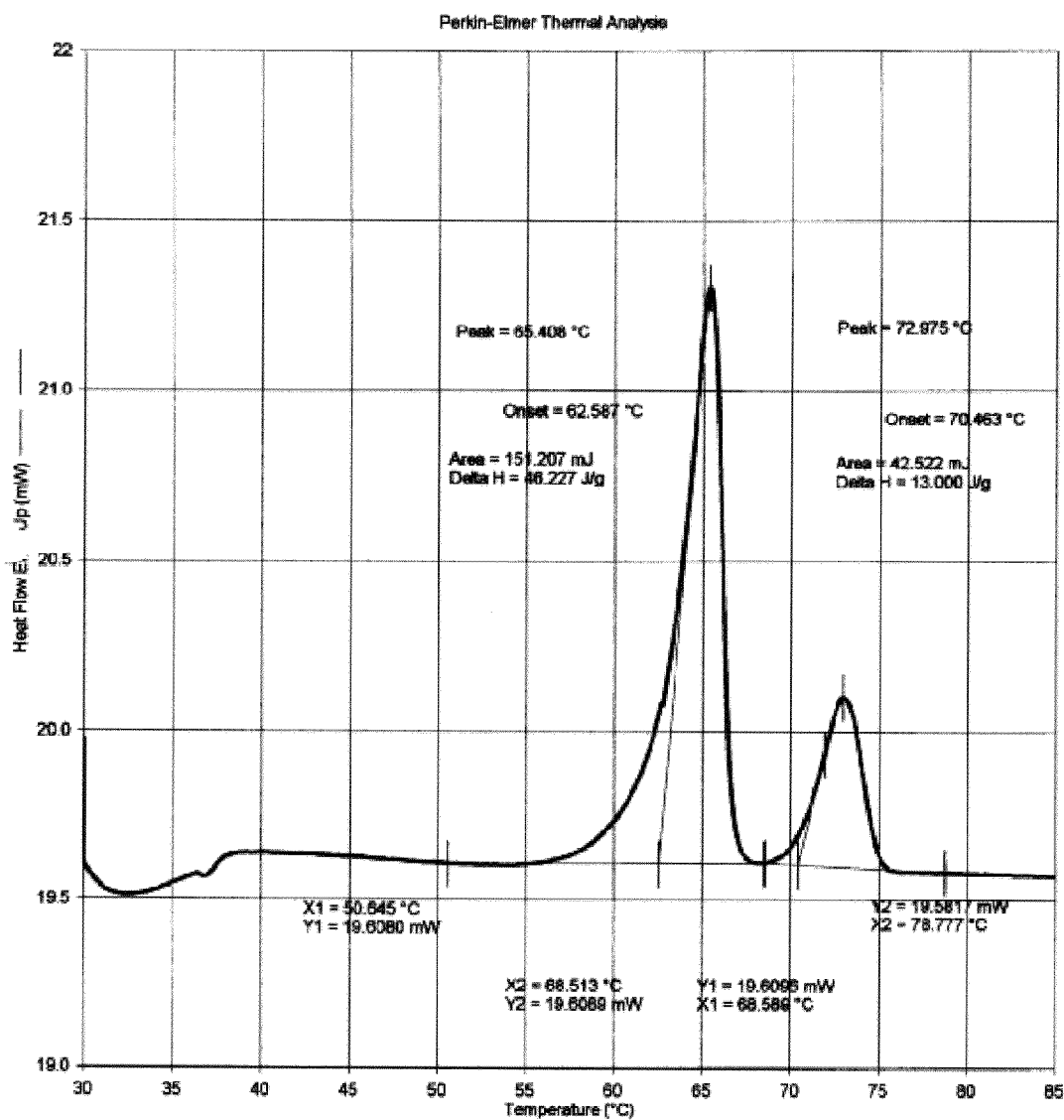
FIG. 7 depicts a thermogram of stress stability sample 2 of lot X10510 subjected to 40° C., ambient air headspace and protected from light exposure.

Spontaneous solid-state polymorphic conversion was observed in a laboratory stress stability study. Two Bimatoprost lots (X11192 and X10510) were subjected to a variety of experimental stress conditions at 40° C. (see Table 6). The experimental design included ambient air and argon headspaces, exposure to fluorescent light, and different surface-to-volume ratios. The 70-day time-point samples were analyzed by HPLC and DSC. The DSC results show that all the samples were polymorph I, except for two samples of lot X10510 that were subjected to ambient air headspace (regardless of light exposure). These samples underwent a partial morphological conversion in which both polymorphs I and II were present simultaneously (see FIGS. 6 and 7).

TABLE 6

Calorimetric results of the laboratory stress stability samples with the lower surface-to-volume ratio (4 mm layer thickness) from bimatoprost lots X11192 and X10510

| Sample | Storage Conditions | ΔH (J/g) | Peak (° C.) | Peak (° C.) |
| --- | --- | --- | --- | --- |
| X11192 | Control (freezer) | 61.2 | 66.8 | — |
| X11192 | 40° C./air/light | 60.4 | 66.9 | — |
| X11192 | 40° C./argon/light | 60.2 | 66.9 | — |
| X11192 | 40° C./air/dark | 61.3 | 67.1 | — |
| X11192 | 40° C./argon/dark | 60.8 | 67.2 | — |
| X10510 | Control (freezer) | 62.4 | 66.3 | — |
| X10510 | 40° C./air/light | 58.0* | ~63 | 71.8 |
| X10510 | 40° C./argon/light | 56.6 | 65.0 | — |
| X10510 | 40° C./air/dark | 59.2* | 65.4 | 73.0 |
| X10510 | 40° C./argon/dark | 58.2 | 63.6 | — |

*Total heats of fusion of both polymorphs I and II

The HPLC results indicate that the samples that showed two thermal transitions were intact bimatoprost and not a degradation product. Three samples were analyzed by infrared spectroscopy (IR), NMR and XRPD to further confirm the identity of each sample. These samples were as follows:
Sample A X10510 API stored at 40° C./75% RH for 3 months; polymorph II
Sample B X10510 API stored at 40° C./light/air headspace for 70 days
Sample C X10510 API control sample stored in freezer (see Table 6); polymorph I
NMR characterization of the samples confirmed that all were intact bimatoprost.

The examination by IR spectroscopy also confirmed that the samples were intact bimatoprost. The differences in the spectra revealed that Samples A and C represented different crystal habits. The IR spectrum of Sample B suggests that the crystal habit is a mixture of Samples A and C. Accordingly, DSC results show that Sample B is partially converted to polymorph II.

Determination of the Aqueous Solubility of Polymorph II

The aqueous solubility of polymorph II was determined by preparing in duplicate a 0.4% suspension of a formal stability sample (lot X10510 stored at 25° C./60% RH for 23 months, confirmed as polymorph II). Temperature Program 1 (hold for 1.0 minute at 30° C. and then heat from 30° C. to 85° C. at 2.0° C. per minute), was used to test the 23-month stability sample by DSC to reconfirm the presence of only polymorph II (which was, indeed, the case). The suspension was allowed to rotate continuously over a weekend. The supernatants were assayed by HPLC using X11192 Secondary Reference Standard to determine the drug contents. The solubility of polymorph II of bimatoprost was found to be 0.3% w/w, which also coincides with the solubility of polymorph I. Thus, there is no difference in terms of aqueous solubility between the two polymorphs. Since the active pharmaceutical ingredient will be used in a formulation at a concentration that is only one-tenth of the aqueous solubility of the active pharmaceutical ingredient (as either polymorph), there is no effect of crystal habit on product characteristics or manufacturing process.

Conclusions

The confirmed polymorphism of bimatoprost has no effect on the physicochemical stability of the liquid formulation, the drug product. The solubility of either polymorph is ten times higher than the drug concentration in the product. No polymorphic conversion or degradation was observed in any of the lots that were stored under the recommended storage conditions.

While this invention has been described with respect to these specific examples, it is understood that other modifications and variations are possible without departing from the spirit of the invention.

What is claimed is:
1. 7-[3,5-dihydroxy-2-(3-hydroxy-5-phenyl-pent-1-enyl)-cyclopentyl]-N-ethyl-hept-5-enamide having the structure

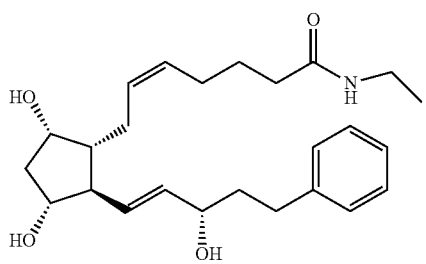 [SMILES: CCNC(=O)CCC/C=C\C[C@@H]1[C@@H](/C=C/[C@@H](O)CCc2ccccc2)[C@H](O)C[C@@H]1O]

in crystalline form II.
2. A crystalline form of 7-[3,5-dihydroxy-2- (3-hydroxy-5-phenyl-pent-1-enyl)- cyclopentyl]-N-ethyl-hept-5-enamide having an X-ray powder diffraction pattern with peaks at (2θ): 3.60, 5.31, 7.09, 10.55, 12.24, 13.29, 14.55, 15.85, 17.60, 18.49, 19.00, 19.65, 21.10, 22.20, 22.69, 24.75 and 28.65.

3. The crystalline form of claim 1 having the X-ray diffraction pattern as shown in FIG. 2.

4. The crystalline form of claim 1 having an endothermic onset at about 70.9 ° C. and a peak at 74.5 ° C. in its differential scanning calorimetry profile.

Figure 1:
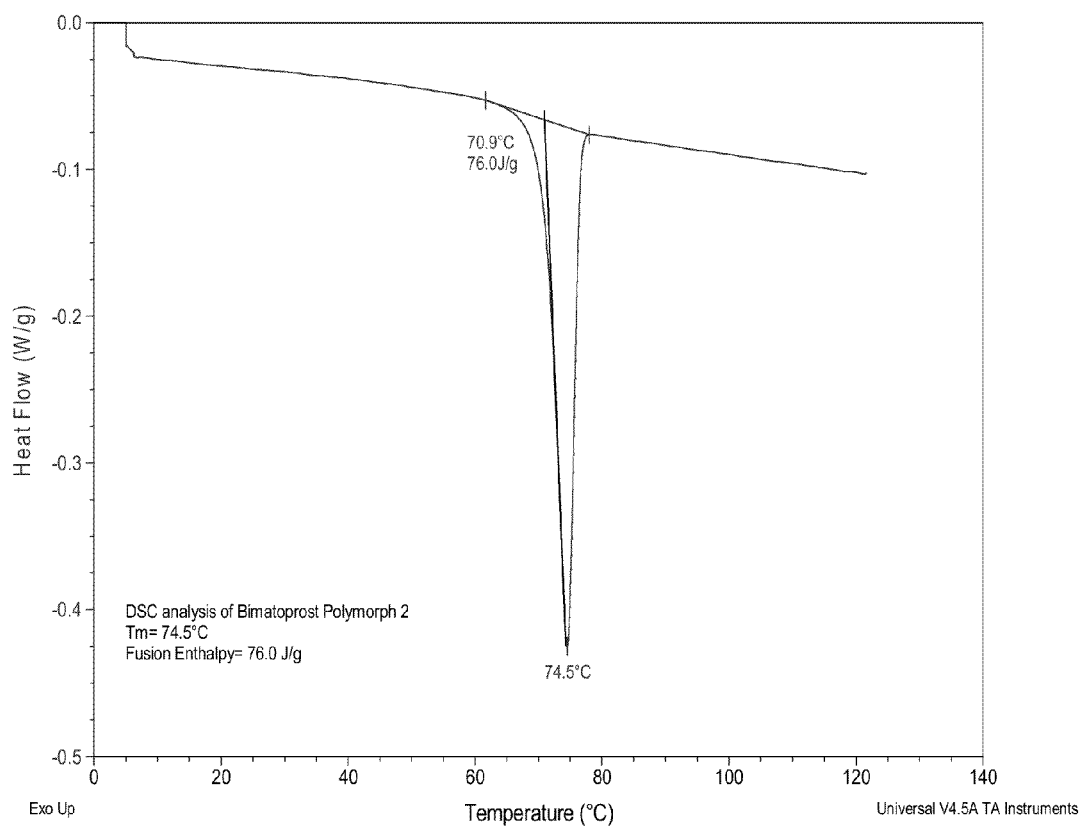
FIG. 1 is a characteristic DSC profile of bimatoprost in crystalline form II.

5. The crystalline form of claim 1 having the DSC profile as shown in FIG. 1.

6. A pharmaceutical composition comprising a therapeutically effective amount of 7-[3,5-dihydroxy-2-(3-hydroxy-5-phenyl-pent-1-enyl)-cyclopentyl]-N-ethyl-hept-5-enamide crystalline form II in an ophthalmically acceptable carrier therefore.

7. The crystalline form of claim 1 free of other crystalline forms.

\* \* \* \* \*